United States Patent
Suzuki et al.

(10) Patent No.: US 8,158,834 B2
(45) Date of Patent: Apr. 17, 2012

(54) METHOD FOR PRODUCING HYDROGENOLYSIS PRODUCT OF POLYHYDRIC ALCOHOL

(75) Inventors: Nobuyoshi Suzuki, Wakayama (JP); Masazumi Tamura, Wakayama (JP)

(73) Assignee: KAO Corporation, Tokyo (JP)

( * ) Notice: Subject to any disclaimer, the term of this patent is extended or adjusted under 35 U.S.C. 154(b) by 0 days.

(21) Appl. No.: 12/863,853

(22) PCT Filed: Jan. 8, 2009

(86) PCT No.: PCT/JP2009/050144
§ 371 (c)(1),
(2), (4) Date: Nov. 1, 2010

(87) PCT Pub. No.: WO2009/093486
PCT Pub. Date: Jul. 30, 2009

(65) Prior Publication Data
US 2011/0040130 A1    Feb. 17, 2011

(30) Foreign Application Priority Data
Jan. 21, 2008    (JP) ................................ 2008-010676

(51) Int. Cl.
*C07C 31/18*    (2006.01)

(52) U.S. Cl. ...................................................... 568/852

(58) Field of Classification Search .................... 568/852
See application file for complete search history.

(56) References Cited

U.S. PATENT DOCUMENTS

| 5,616,817 A | 4/1997 | Schuster et al. |
| 2010/0113841 A1 | 5/2010 | Suzuki et al. |

FOREIGN PATENT DOCUMENTS

| JP | 8 208541 | 8/1996 |
| JP | 2008 44874 | 2/2008 |
| WO | WO 2005/095536 A2 | 10/2005 |
| WO | WO 2005/095536 A3 | 10/2005 |
| WO | WO 2007/053705 A2 | 5/2007 |
| WO | WO 2007/053705 A3 | 5/2007 |
| WO | 2007 129560 | 11/2007 |

OTHER PUBLICATIONS

Extended European Search Report issued Apr. 14, 2011, in European Patent Application No. 09703680.0.

*Primary Examiner* — Sikarl Witherspoon
(74) *Attorney, Agent, or Firm* — Oblon, Spivak, McClelland, Maier & Neustadt, L.L.P.

(57) ABSTRACT

The present invention relates to a process for producing a hydrogenolysis product of a polyhydric alcohol in an efficient manner. The present invention provides a process for producing a hydrogenolysis product of a polyhydric alcohol in a batch manner in which the hydrogenolysis reaction is carried out while removing water retained in a liquid phase of a reaction system.

16 Claims, No Drawings

METHOD FOR PRODUCING HYDROGENOLYSIS PRODUCT OF POLYHYDRIC ALCOHOL

CROSS REFERENCE TO RELATED APPLICATION

This application is a 371 of PCT/JP09/050144, filed on Jan. 8, 2009, and claims priority to Japanese Patent Application No. 2008-010676, filed on Jan. 21, 2008.

FIELD OF THE INVENTION

The present invention relates to a process for producing hydrogenolysis products of polyhydric alcohols with a high selectivity by converting the polyhydric alcohols into the aimed products in an efficient manner.

BACKGROUND OF THE INVENTION

Hydrogenolysis of polyhydric alcohols obtained from the natural world using a catalyst for converting the polyhydric alcohols into other compounds is an important technique from the viewpoint of effective utilization of materials or substances.

On the other hand, production of glycerol used as the polyhydric alcohol in food or medical applications has been increased year by year. One of the reasons therefor is the spread of bio-diesel fuels which have recently come to dominate owing to uncertain supply of fossil fuels or global warming problems. Glycerol is produced during the process for production of the bio-diesel fuels from raw vegetable materials. However, excessive supply of the glycerol has occurred due to currently limited applications thereof. Therefore, effective utilization of the glycerol has been demanded. As one solution of the above problem, a catalytic reaction of the glycerol for converting the glycerol into C3 alcohols has been noticed over the world.

The C3 alcohols are useful as various industrial materials, etc. Among the C3 alcohols, as diols, there are 1,3-propanediol and 1,2-propanediol. The 1,3-propanediol has been noticed as a raw material of polyesters and polyurethanes, etc.

On the other hand, the 1,2-propanediol (hereinafter occasionally referred to merely as "1,2-PD") has been used, for example, for production of polyester resins, paints, alkyd resins, various plasticizers, anti-freezing fluids, brake oils, etc., and further are useful for production of food wetting agents, viscosity increasers for fruit juices, cellophane softeners for food, cosmetics, drugs, etc.

In order to effectively utilize glycerol, there have been proposed various methods for producing 1,2-PD by hydrogenolysis of the glycerol.

For example, as the hydrogenolysis of glycerol using a catalyst, there are known (1) the method using a nickel-rhenium/carbon catalyst (for example, refer to Patent Document 1), (2) the method using a ruthenium/carbon catalyst (for example, refer to Patent Document 2), (3) the method using a copper-zinc/alumina catalyst (for example, refer to Patent Document 3), (4) the method using a copper-zinc oxide catalyst (for example, refer to Patent Document 4), (5) the method using a copper-chromium catalyst (for example, refer to Non-Patent Document 1), (6) the method using a ruthenium catalyst (for example, refer to Patent Document 5), and the like.

However, these conventional methods are still unsatisfactory because of a low conversion rate of glycerol, a low selectivity to 1,2-PD, etc. In particular, under the low-pressure condition which is generally advantageous for practicing industrial methods, it tends to be difficult to achieve both a high reactivity of the glycerol and a high selectivity to 1,2-PD. Thus, the conventional methods have failed to attain satisfactory levels of the reactivity and the selectivity. In addition, in Non-Patent Document 1 and Patent Document 5, there is described such an effect of water that the selectivity to the aimed product is considerably deteriorated if no water is previously added to the reaction system.

Patent Document 1: PCT Pamphlet WO 03/035582
Patent Document 2: EP-A 523014
Patent Document 3: EP-A 523015
Patent Document 4: DP-A 4302464
Patent Document 5: JP-A 2007-283175
Non-Patent Document 1: Applied Catalysis A: General, 281, 225, (2005)

SUMMARY OF THE INVENTION

The present invention relates to a process for producing a hydrogenolysis product of a polyhydric alcohol using a catalyst by a batch method in which a reactivity of the polyhydric alcohol is enhanced. In particular, the technical task of the present invention resides in that when using glycerol as the polyhydric alcohol, a reactivity of glycerol is enhanced so that the glycerol is effectively converted into 1,2-propanediol.

The present inventors have found that the above object or task of the present invention can be achieved by the process for producing a hydrogenolysis product of a polyhydric alcohol in which the reaction is allowed to proceed while removing water retained in a liquid phase of a reaction system during proceeding of the reaction.

Thus, the present invention relates to (1) a process for producing a hydrogenolysis product of a polyhydric alcohol by a batch method which includes the step of contacting and reacting the polyhydric alcohol with hydrogen in the presence of a hydrogenolysis catalyst while removing water contained in a liquid phase of a reaction system.

DETAILED DESCRIPTION OF THE INVENTION

In the process for producing a hydrogenolysis product of a polyhydric alcohol according to the present invention, the polyhydric alcohol and hydrogen are heated in the presence of a hydrogenolysis catalyst to hydrogenolyze the polyhydric alcohol.

The polyhydric alcohol is preferably in the form of a compound having 2 to 6 hydroxyl groups. More specifically, the polyhydric alcohol include aliphatic or alicyclic polyhydric alcohols having 2 to 6 hydroxyl groups and 2 to 60 carbon atoms. Specific examples of the polyhydric alcohol include ethylene glycol, diethylene glycol, triethylene glycol, polyethylene glycol, various propanediols, various dipropanediols, various tripropanediols, various butanediols, various dibutanediols, various pentanediols, various pentanetriols, various hexanediols, various hexanetriols, glycerol, diglycerol, triglycerol, various cyclohexanediols, various cyclohexanetriols, pentaerythritol, trimethylol propane, and sugar alcohols such as sorbitol and mannitol. Among these polyhydric alcohols, from the industrial viewpoints, preferred are glycerol and sugar alcohols such as sorbitol and mannitol are preferred, and especially preferred is glycerol.

The hydrogenolysis product of the polyhydric alcohol as mentioned in the present invention means a compound obtained by reacting the polyhydric alcohol with hydrogen to decompose hydroxyl groups thereof to such an extent that at least one of the hydroxyl groups remains in a non-decomposed state. For example, the hydrogenolysis product of glycerol (number of hydroxyl groups in molecule: 3) includes a C3 diol (number of hydroxyl groups in molecule: 2) and a C3 monool (number of hydroxyl groups in molecule: 1).

As the above hydrogenolysis catalyst, there may be used, for example, at least one metal selected from the group consisting of copper, nickel, cobalt, ruthenium, palladium, platinum, rhodium, etc., or a complex catalyst containing any one or more of these metal atoms. Also, the hydrogenolysis catalyst may be in the form of a solid catalyst prepared by supporting any of these metals on a carrier such as alumina, silica and titanium oxide. Among these catalysts, preferred are copper-containing catalysts (hereinafter occasionally referred to merely as "copper catalysts"), and especially preferred are copper-iron-aluminum catalysts, copper/silica catalysts, copper-zinc/titanium oxide catalysts and copper-Raney catalysts. In addition, among these catalysts, more preferred are copper-iron-aluminum catalysts and copper/silica catalysts, and especially preferred are copper/silica catalysts.

As the hydrogenolysis catalyst, there may also be used commercially available catalysts. Further, the hydrogenolysis catalyst may be prepared by supporting the metal component on the carrier by conventionally known methods such as, for example, a precipitation method, an ion-exchange method, an evaporation-to-dryness method, a spray drying method and a kneading method which have been usually used for the above purposes.

The amount of the hydrogenolysis catalyst used is from 0.01 to 20 parts by mass, preferably from 0.1 to 10 parts by mass and more preferably from 0.3 to6 parts by mass on the basis of 100 parts by mass of the polyhydric alcohol as the raw material.

In the process for producing the hydrogenolysis product of the polyhydric alcohol according to the present invention, water being present in a liquid phase of the reaction system may be removed by the method of allowing the water being present in the liquid phase to be induced into a vapor phase in the form of water vapor, or the method of previously placing a dehydrating agent in a reaction vessel to absorb the water being present in the liquid phase therewith. In the former method of allowing the water being present in the liquid phase to be induced into a vapor phase in the form of water vapor, the removal of water may be promoted by flowing a gas through the reaction vessel to induce the water out of the reaction vessel. In this case, as the gas to be flowed through the reaction vessel, there may be used at least one gas selected from the group consisting of hydrogen, and inert gases such as nitrogen and argon. In the present invention, the removal of water is preferably promoted by flowing the gas through the reaction vessel. Further, as the gas to be flowed through the reaction vessel, a hydrogen gas is preferred because hydrogen is used as a reagent to be reacted.

In the present invention, it is not necessary to continuously remove water from the reaction system. The reaction efficiency can be enhanced only by removing a part of water from the reaction system. The reaction efficiency as used herein mainly means a reaction rate. As far as glycerol is concerned, the reaction efficiency also means a conversion rate of glycerol into 1,2-propanediol. In the hydrogenolysis, water is produced from the polyhydric alcohol. In the batch reaction system, since water is accumulated in the reaction system, the amount of water being present in the reaction system is increased as the reaction proceeds. On the other hand, the amount of the polyhydric alcohol in the reaction system is decreased as the reaction proceeds. The total amount of water finally produced may be determined from the amount of the polyhydric alcohol used in the reaction, although it varies depending upon the kind of the polyhydric alcohol used.

In the present invention, the removal of water from the liquid phase of the reaction system can be suitably carried out at any time between a time at which 60 mol % of the polyhydric alcohol in the liquid phase of the reaction system is reacted, in other words, a time at which the amount of the residual polyhydric alcohol in the liquid phase reaches 40 mol %, and a time at which the polyhydric alcohol is completely reacted, such that a proportion of water being present in the liquid phase of the reaction system (hereinafter occasionally referred to merely as a "water ratio") is 0.5 or less, preferably 0.4 or less and more preferably 0.3 or less, assuming that a total amount of water generated from the polyhydric alcohol is 1. The amount of water being present in the reaction system is preferably as small as possible, and the water is preferably continuously driven out of the reaction system. In order to start the remove of water from an initial stage of the reaction, the above method of flowing a gas through the reaction vessel is preferably used to remove water from the liquid phase of the reaction system. From the numerical viewpoint, after the time at which 60 mol % of the polyhydric alcohol in the liquid phase of the reaction system is reacted, the proportion of water being present in the liquid phase of the reaction system is preferably maintained in the range of 0.5 or less, more preferably 0.4 or less and still more preferably 0.3 or less, assuming that a total amount of water generated from the polyhydric alcohol is 1.

In particular, in the reaction for converting glycerol into 1,2-propanediol, as the amount of water being present in the liquid phase of the reaction system is decreased, the reaction efficiency of glycerol is increased. The amount of water being present in the liquid phase of the reaction system may be calculated from the value measured by subjecting a sample withdrawn from the liquid phase of the reaction system with time to Karl Fischer analysis.

The reaction conditions are not particularly limited, and may be appropriately determined according to kinds of polyhydric alcohol and catalyst used in the reaction. In general, the hydrogen pressure is preferably 30 MPa or less as measured at ordinary temperature. From the industrial viewpoints, the hydrogen pressure is preferably even lower, i.e., in the range of from 0.1 to 10 MPa, more preferably from 0.5 to 5 MPa and still more preferably from 0.5 to 3 MPa. The reaction temperature of 80° C. or higher is usually sufficient to carry out the hydrogenolysis. From the viewpoints of a good conversion rate of the polyhydric alcohol by hydrogenolysis as well as a good selectivity to the aimed hydrogenolysis product, the reaction temperature is preferably in the range of from 130 to 350° C., more preferably from 160 to 300° C. and still more preferably from 180 to 250° C.

The reaction apparatus used in the hydrogenolysis reaction is preferably a pressure apparatus of a batch type such as an autoclave.

In the process for producing the hydrogenolysis product of the polyhydric alcohol according to the present invention, glycerol is preferably used as the polyhydric alcohol. When using glycerol as the polyhydric alcohol, 1,2-PD can be produced as the hydrogenolysis product thereof in an efficient manner.

EXAMPLES

Example 1

(Production of Copper-Iron-Aluminum-Based Catalyst)

The following procedure was conducted to produce a copper-iron-aluminum-based catalyst having an atomic ratio copper/iron/aluminum of 1/0.8/1.8.

A reactor equipped with a reflux condenser was charged with water (300 g), $CuSO_4.5H_2O$ (48 g), $FeSO_4.7H_2O$ (46.8 g) and aluminum hydroxide (12.8 g), and the contents in the reactor were heated to 96° C. while stirring. While maintaining an inside of the reactor at a temperature of 95° C.±2° C., the contents in the reactor were allowed to stand for 1 h. Next, while maintaining the same temperature, a solution prepared by dissolving $Na_2CO_3$ (44.8 g) in water (150 g) was added dropwise into the reactor over about 80 min. Further, while maintaining the inside of the reactor at a temperature of 95° C.±2° C., a solution prepared by dissolving $CuSO_4.5H_2O$ (4.8 g) and $Al_2(SO_4)_3.16H_2O$ (46.8 g) in water (109.2 g) and a solution prepared by dissolving $Na_2CO_3$ (27.6 g) in water (98.2 g) were added dropwise at the same time into the reactor. At this time, the former aqueous solution of the metal salts was added dropwise over 60 min, whereas the latter aqueous solution of the alkali substance was added dropwise over 30 min. Next, a solution prepared by dissolving $Al_2(SO_4)_3.16H_2O$ (23.4 g) in water (53.5 g) was added dropwise into the reactor over 30 min, and then a solution prepared by dissolving $Na_2CO_3$ (14.3 g) in water (54.9 g) was added dropwise into the reactor over 30 min. Further, a 10% NaOH aqueous solution was added dropwise into the reactor to adjust a pH of the mixture in the reactor to 10.5. While maintaining a pH of the mixture in the reactor at 10.5, the mixture was aged for 1 h. After completion of the aging, the obtained reaction mixture was subjected to suction filtration. The resulting precipitate was repeatedly washed three times with water in an amount of 450 mL for each time, and then dried at 100° C. The resulting dried product was lightly pulverized and then calcined in air at 750° C. for 1 h, thereby obtaining a copper-iron-aluminum-based catalyst supported on an alumina carrier.

(Hydrogenolysis)

A 500 mL autoclave made of iron and equipped with a stirrer was charged with 10 g of the above-prepared copper-iron-aluminum-based catalyst and 200 g of glycerol, and an inside of the autoclave was purged with hydrogen. Thereafter, hydrogen was introduced into a liquid in the autoclave and flowed therethrough at a rate of 5 L/min (25° C., $H_2$) while maintaining an inside pressure in the autoclave at 2 MPa, and the contents of the autoclave were heated and reacted with each other at 230° C. Water in the liquid phase was removed in the form of water vapor through a discharge port provided at an upper portion of the iron autoclave out of the reaction vessel.

The respective samples withdrawn from the reaction system with time as well as the reaction solution obtained after completion of the reaction were subjected to filtration, and then subjected to Karl Fischer analysis to measure an amount of water contained therein and further to gas chromatography under the following conditions to conduct a quantitative determination of the reaction product. From the thus measured values, the amount (mol %) of residual glycerol as well as the proportion of water being present in the liquid phase of the reaction system assuming that the total amount of water generated from glycerol is 1 were determined. In addition, the first order reaction rate constant k was calculated from the amounts of the residual glycerol measured with time, and used as a scale for the reaction rate.

As a result, it was confirmed that the values of selectivity to the final reaction products were respectively 93 mol % for 1,2-PD, 3 mol % for ethylene glycol (hereinafter referred to merely as "EG"), and 4 mol % for others and unknown substances. The results are shown in Table 1.

[Gas Chromatography]

Column: "Ultra-alloy capillary column", 15.0 m×250 μm×0.15 μm (available from Frontier Laboratories Inc.); Detector: FID; Injection temperature: 300° C.; Detector temperature: 350° C.; Flow rate of He: 4.6 mL/min Examples 2 and 3

The hydrogenolysis reaction was carried out under the conditions shown in Tables 1 and 6 by using the catalyst produced in Example 1. More specifically, in Example 2, the flow rate of hydrogen was reduced from 5 L/min to 1 L/min. Whereas, in Example 3, hydrogen was flowed and introduced not into a liquid phase but into a vapor phase being present above the reaction solution to induce water vapor in the vapor phase out of the reaction vessel, so that an additional amount of water vapor was fed from the liquid phase to thereby enable indirect removal of water from the liquid phase. The results are shown in Table 1.

TABLE 1

| | | Examples | | | | | | |
|---|---|---|---|---|---|---|---|---|
| | | 1 | | | 2 | | | 3 |
| Catalyst | | $Cu\text{—}Fe\text{—}Al_2O_3$ | | | $Cu\text{—}Fe\text{—}Al_2O_3$ | | | $Cu\text{—}Fe\text{—}Al_2O_3$ |
| Amount of catalyst used (based on 100 parts by mass of glycerol) | | 5 parts by mass | | | 5 parts by mass | | | 5 parts by mass |
| Glycerol as raw material/water (molar ratio) | | 1/0 | | | 1/0 | | | 1/0 |
| Reaction pressure (MPa) | | 2.0 | | | 2.0 | | | 2.0 |
| Reaction temperature (° C.) | | 230 | | | 230 | | | 230 |
| Flowing conditions of hydrogen | Flow rate (25° C., 0.1 MPa) | 5 L/min | | | 1 L/min | | | 5 L/min |
| | Flowing method | Introduced into liquid | | | Introduced into liquid | | | Introduced into vapor phase |

| | | Residual glycerol (mol %) | k ($h^{-1}$) | Amount of water in reaction liquid*[1] | Residual glycerol (mol %) | k ($h^{-1}$) | Amount of water in reaction liquid*[1] | Residual glycerol (mol %) | k ($h^{-1}$) | Amount of water in reaction liquid*[1] |
|---|---|---|---|---|---|---|---|---|---|---|
| After reacted for 1 h | | 66.2 | | 0.17 | 66.0 | | 0.26 | 77.6 | | 0.23 |
| After reacted for 2 h | | 44.3 | 0.40 | 0.06 | 47.2 | 0.34 | 0.42 | 53.4 | 0.37 | 0.28 |
| After reacted for 3 h | | 23.2 | 0.65 | 0.04 | 34.1 | 0.33 | 0.47 | 37.1 | 0.36 | 0.14 |
| After reacted for 4 h | | 5.7 | 1.40 | 0.03 | 24.5 | 0.33 | 0.44 | 22.0 | 0.52 | 0.10 |
| After reacted for 5 h | | 0.7 | 2.10 | 0.01 | 18.7 | 0.27 | 0.38 | 11.6 | 0.64 | 0.10 |
| After reacted for 6 h | | | | | 14.5 | 0.25 | 0.34 | 4.3 | 0.99 | 0.05 |
| After reacted for 7 h | | | | | 9.7 | 0.40 | 0.24 | 0.8 | 1.68 | 0.03 |
| After reacted for 8 h | | | | | 6.5 | 0.40 | 0.15 | | | |
| Selectivity to final reaction products (mol %) | 1,2-PD | | 93 | | | 81 | | | 90 | |
| | EG | | 3 | | | 3 | | | 4 | |
| | Others and unknown substances | | 4 | | | 16 | | | 6 | |

Note

*[1] Amount of water in reaction liquid is the value assuming that a total amount of water generated from glycerol is 1.

Example 4

(Copper-Raney Catalyst)

The same procedure as in Example 1 was repeated except for using a copper-Raney catalyst (product number: "RC-300") available from NIKKO RICA CORPORATION.

Example 5

(Production of Copper-Zinc/Titanium Oxide Catalyst)

A reactor was charged with copper nitrate (100 g) and zinc nitrate (30 g), and the contents in the reactor were dissolved in water (2,000 g). The resulting solution was heated while stirring. Next, titanium oxide (33 g) was charged into the reactor at 50° C., and then the contents in the reactor were heated to 90° C. at which a 10 mass % $Na_2CO_3$ aqueous solution (546 g) (amount of $Na_2CO_3$ added: equimolar amount based on the metal salts) was added dropwise into the reactor over 1 h. After aging the contents in the reactor for 1 h, the resulting precipitate was separated therefrom, washed with water, dried at 110° C. for 10 h, and then calcined at 600° C. for 1 h. As a result, it was confirmed that the atomic ratio of copper to zinc (copper/zinc) in the thus obtained metal oxide was 4/1, and the amount of the metal oxide supported on titanium oxide as a carrier was 50% by mass on the basis of the titanium oxide. The hydrogenolysis reaction was carried out in the same manner as in Example 1 except for using the thus obtained titanium oxide-supported copper/zinc oxide catalyst.

The results of Examples 4 and 5 are shown in Table 2.

TABLE 2

|  |  | Examples | |
| --- | --- | --- | --- |
|  |  | 4 | 5 |
| Catalyst |  | Cu-Raney | Cu—Zn/$TiO_2$ |
| Amount of catalyst used (based on 100 parts by mass of glycerol) |  | 5 parts by mass | 5 parts by mass |
| Glycerol as raw material/water (molar ratio) |  | 1/0 | 1/0 |
| Reaction pressure (MPa) |  | 2.0 | 2.0 |
| Reaction temperature (° C.) |  | 230 | 230 |
| Flowing conditions of hydrogen | Flow rate (25° C., 0.1 MPa) | 5 L/min | 5 L/min |
|  | Flowing method | Introduced into liquid | Introduced into liquid |

|  |  | Residual glycerol (mol %) | k ($h^{-1}$) | Amount of water in reaction liquid*[1] | Residual glycerol (mol %) | k ($h^{-1}$) | Amount of water in reaction liquid*[1] |
| --- | --- | --- | --- | --- | --- | --- | --- |
| After reacted for 1 h |  | 51.6 |  | 0.42 | 74.5 |  | 0.22 |
| After reacted for 2 h |  | 29.3 | 0.57 | 0.14 | 54.7 | 0.31 | 0.09 |
| After reacted for 3 h |  |  |  |  |  |  |  |
| After reacted for 4 h |  | 0.9 | 1.74 | 0.02 | 27.3 | 0.35 | 0.04 |
| After reacted for 5 h |  |  |  |  |  |  |  |
| After reacted for 6 h |  |  |  |  | 3.1 | 1.09 | 0.02 |
| After reacted for 7 h |  |  |  |  |  |  |  |
| After reacted for 8 h |  |  |  |  | 0.1 | 1.72 | 0.03 |
| Selectivity to final reaction products (mol %) | 1,2-PD |  | 79 |  |  | 75 |  |
|  | EG |  | 3 |  |  | 6 |  |
|  | Others and unknown substances |  | 18 |  |  | 19 |  |

Note

*[1]Amount of water in reaction liquid is the value assuming that a total amount of water generated from glycerol is 1.

Examples 6 to 11

(Copper/Silica Catalyst)

Using a pulverized product of a copper/silica catalyst (product number: "F01B") having an atomic ratio Cu/Si of 1/0.55 available from Nikki Chemical Co., Ltd., the hydrogenolysis reaction was carried out under the conditions shown in Tables 3 and 4. In Examples 6 to 9, the copper/silica catalyst was used in an amount of 5 parts by mass, 2 parts by mass, 1 part by mass and 0.5 part by mass, respectively, on the basis of 100 parts by mass of glycerol, whereas in Examples 6, 10 and 11, the reaction was carried out at a temperature of 230° C., 220° C. and 200° C., respectively, to thereby confirm whether or not any influences were caused by the change in these factors. The results are shown in Tables 3 and 4.

TABLE 3

|  |  | Examples | | | | | | | |
|---|---|---|---|---|---|---|---|---|---|
|  |  | 6 | | | 7 | | | 8 | | |
| Catalyst | | Cu/Silica | | | Cu/Silica | | | Cu/Silica | | |
| Amount of catalyst used (based on 100 parts by mass of glycerol) | | 5 parts by mass | | | 2 parts by mass | | | 1 part by mass | | |
| Glycerol as raw material/water (molar ratio) | | 1/0 | | | 1/0 | | | 1/0 | | |
| Reaction pressure (MPa) | | 2.0 | | | 2.0 | | | 2.0 | | |
| Reaction temperature (° C.) | | 230 | | | 230 | | | 230 | | |
| Flowing conditions of hydrogen | Flow rate (25° C., 0.1 MPa) | 5 L/min | | | 5 L/min | | | 5 L/min | | |
|  | Flowing method | Introduced into liquid | | | Introduced into liquid | | | Introduced into liquid | | |
|  |  | Residual glycerol (mol %) | k ($h^{-1}$) | Amount of water in reaction liquid*[1] | Residual glycerol (mol %) | k ($h^{-1}$) | Amount of water in reaction liquid*[1] | Residual glycerol (mol %) | k ($h^{-1}$) | Amount of water in reaction liquid*[1] |
| After reacted for 1 h | | 50.1 |  | 0.21 | 62.5 |  | 0.21 | 78.1 |  | 0.17 |
| After reacted for 2 h | | 16.2 | 1.13 | 0.05 |  |  |  | 57.7 | 0.30 | 0.05 |
| After reacted for 3 h | | 0.4 | 3.70 | 0.02 | 12.4 | 0.81 | 0.05 | 34.8 | 0.51 | 0.02 |
| After reacted for 4 h | |  |  |  | 0.5 | 3.21 | 0.01 | 20.0 | 0.55 | 0.02 |
| After reacted for 5 h | |  |  |  |  |  |  | 12.5 | 0.47 | 0.02 |
| After reacted for 6 h | |  |  |  |  |  |  | 3.0 | 1.43 | 0.02 |
| After reacted for 7 h | |  |  |  |  |  |  | 0.5 | 1.79 | 0.01 |
| After reacted for 8 h | |  |  |  |  |  |  | 0.1 | 1.61 | 0.01 |
| After reacted for 10 h | |  |  |  |  |  |  |  |  |  |
| Selectivity to final reaction products (mol %) | 1,2-PD | 93 | | | 92 | | | 91 | | |
|  | EG | 5 | | | 4 | | | 4 | | |
|  | Others and unknown substances | 2 | | | 4 | | | 5 | | |

Note
*[1] Amount of water in reaction liquid is the value assuming that a total amount of water generated from glycerol is 1.

TABLE 4

|  |  | Examples | | |
|---|---|---|---|---|
|  |  | 9 | 10 | 11 |
| Catalyst | | Cu/Silica | Cu/Silica | Cu/Silica |
| Amount of catalyst used (based on 100 parts by mass of glycerol) | | 0.5 part by mass | 5 parts by mass | 5 parts by mass |
| Glycerol as raw material/water (molar ratio) | | 1/0 | 1/0 | 1/0 |
| Reaction pressure (MPa) | | 2.0 | 2.0 | 2.0 |
| Reaction temperature (° C.) | | 230 | 220 | 200 |
| Flowing conditions of | Flow rate (25° C., 0.1 MPa) | 5 L/min | 5 L/min | 5 L/min |

TABLE 4-continued

| hydrogen | Flowing method | Introduced into liquid | | | Introduced into liquid | | | Introduced into liquid | | |
|---|---|---|---|---|---|---|---|---|---|---|
| | | Residual glycerol (mol %) | k (h$^{-1}$) | Amount of water in reaction liquid*[1] | Residual glycerol (mol %) | k (h$^{-1}$) | Amount of water in reaction liquid*[1] | Residual glycerol (mol %) | k (h$^{-1}$) | Amount of water in reaction liquid*[1] |
| After reacted for 1 h | | 78.4 | | 0.14 | 71.5 | | 0.20 | 88.6 | | 0.12 |
| After reacted for 2 h | | | | | 42.2 | 0.53 | 0.09 | 74.5 | 0.17 | 0.11 |
| After reacted for 3 h | | 50.8 | 0.22 | 0.05 | | | | | | |
| After reacted for 4 h | | | | | 2.6 | 1.39 | 0.04 | 38.7 | 0.33 | 0.05 |
| After reacted for 5 h | | 31.7 | 0.24 | 0.03 | | | | | | |
| After reacted for 6 h | | | | | 0.1 | 1.63 | 0.01 | 12.2 | 0.58 | 0.04 |
| After reacted for 7 h | | | | | | | | | | |
| After reacted for 8 h | | 10.3 | 0.37 | 0.02 | | | | 2.0 | 0.90 | 0.02 |
| After reacted for 10 h | | 3.5 | 1.08 | 0.02 | | | | | | |
| Selectivity to final reaction products (mol %) | 1,2-PD | | 89 | | | 89 | | | 96 | |
| | EG | | 4 | | | 4 | | | 3 | |
| | Others and unknown substances | | 7 | | | 7 | | | 1 | |

Note
*[1]Amount of water in reaction liquid is the value assuming that a total amount of water generated from glycerol is 1.

Comparative Examples 1 to 6

A 500 mL autoclave made of iron and equipped with a stirrer was charged with 200 g of glycerol as a raw material and with a pulverized product of a copper/silica catalyst (product number: "F01B") available from Nikki Chemical Co., Ltd., in an amount of 5 parts by mass on the basis of 100 parts by mass of glycerol, and an inside of the autoclave was purged with hydrogen. Then, as shown in Tables 5 and 6, hydrogen was introduced into the autoclave at room temperature until a hydrogen pressure therein reached 1 MPa. After the contents in the autoclave were heated to the respective temperatures as shown in the Tables, the hydrogen pressure in the autoclave was raised until reaching 6 MPa in Comparative Examples 1 to 3, 2 MPa in Comparative Example 4, and 15 MPa in Comparative Examples 5 and 6, respectively. Thereafter, the autoclave was kept in a hermetically sealed condition without flowing hydrogen therethrough, and under such a condition, the hydrogenolysis reaction was carried out while maintaining a constant hydrogen pressure within the autoclave by compensating an amount of hydrogen consumed and decreased by the reaction. Incidentally, in Comparative Example 2, the reaction was carried out using a solution having a molar ratio of water to the raw glycerol of 1/1.3, whereas in Comparative Examples 3 and 6, the reaction was carried out using a solution having a molar ratio of water to the raw glycerol of 100/20.5.

TABLE 5

| | | Comparative Examples | |
|---|---|---|---|
| | | 1 | 2 |
| Catalyst | | Cu/Silica | Cu/Silica |
| Amount of catalyst used (based on 100 parts by mass of glycerol) | | 5 parts by mass | 5 parts by mass |
| Glycerol as raw material/water (molar ratio) | | 1/0 | 1/1.3 |
| Reaction pressure (MPa) | | 6.0 | 6.0 |
| Reaction temperature (° C.) | | 230 | 230 |
| Flowing conditions of hydrogen | Flow rate (25° C., 0.1 MPa) Flowing method | (Under hermetically sealed condition) | (Under hermetically sealed condition) |
| | | Residual glycerol (mol %) | k (h$^{-1}$) | Amount of water in reaction liquid*[1] | Residual glycerol (mol %) | k (h$^{-1}$) | Amount of water in reaction liquid*[1] |
| After reacted for 1 h | | 55.9 | | 0.44 | | | |
| After reacted for 2 h | | 41.1 | 0.31 | 0.59 | 67.0 | | 1.53 |
| After reacted for 3 h | | 29.6 | 0.33 | 0.64 | | | |
| After reacted for 4 h | | 22.8 | 0.26 | 0.70 | 44.4 | 0.21 | 1.78 |
| After reacted for 5 h | | 17.6 | 0.26 | 0.72 | | | |
| After reacted for 6 h | | 13.1 | 0.30 | 0.74 | 32.9 | 0.15 | 1.93 |

TABLE 5-continued

| | | | | | | |
|---|---|---|---|---|---|---|
| After reacted for 7 h | | | | | | |
| After reacted for 8 h | | 8.8 | 0.20 | 0.87 | 25.3 | 0.13 | 2.02 |
| After reacted for 11 h | | | | | | |
| After reacted for 14 h | | | | | | |
| After reacted for 22 h | | | | | | |
| After reacted for 26 h | | | | | | |
| After reacted for 30 h | | | | | | |
| Selectivity to final reaction products (mol %) | 1,2-PD | | 90 | | | 89 | |
| | EG | | 5 | | | 6 | |
| | Others and unknown substances | | 5 | | | 5 | |

| | Comparative Examples | |
|---|---|---|
| | 3 | 4 |
| Catalyst | Cu/Silica | Cu/Silica |
| Amount of catalyst used (based on 100 parts by mass of glycerol) | 5 parts by mass | 5 parts by mass |
| Glycerol as raw material/water (molar ratio) | 1/20.5 | 1/0 |
| Reaction pressure (MPa) | 6.0 | 2.0 |
| Reaction temperature (° C.) | 230 | 220 |
| Flowing conditions of hydrogen | (Under hermetically sealed condition) | (Under hermetically sealed condition) |
| Flow rate (25° C., 0.1 MPa) | | |
| Flowing method | | |

| | Residual glycerol (mol %) | k (h$^{-1}$) | Amount of water in reaction liquid*[1] | Residual glycerol (mol %) | k (h$^{-1}$) | Amount of water in reaction liquid*[1] |
|---|---|---|---|---|---|---|
| After reacted for 1 h | 93.7 | | 21.00 | | | |
| After reacted for 2 h | 89.9 | 0.04 | 20.96 | 66.8 | | 0.44 |
| After reacted for 3 h | 85.4 | 0.05 | 20.88 | | | |
| After reacted for 4 h | | | | 56.8 | 0.08 | 0.50 |
| After reacted for 5 h | 77.9 | 0.05 | 21.44 | | | |
| After reacted for 6 h | | | | | | |
| After reacted for 7 h | | | | 42.2 | 0.1 | 0.58 |
| After reacted for 8 h | | | | | | |
| After reacted for 11 h | | | | 32.0 | 0.07 | 0.71 |
| After reacted for 14 h | | | | 27.0 | 0.06 | 0.68 |
| After reacted for 22 h | | | | 18.4 | 0.05 | 0.83 |
| After reacted for 26 h | | | | 14.4 | 0.06 | 0.85 |
| After reacted for 30 h | | | | 12.3 | 0.04 | 0.93 |
| Selectivity to final reaction products (mol %) 1,2-PD | | 95 | | | 88 | |
| EG | | 4 | | | 3 | |
| Others and unknown substances | | 1 | | | 9 | |

Note
*[1]Amount of water in reaction liquid is the value assuming that a total amount of water generated from glycerol is 1.

Examples 1, 4, 5 and 6 which were carried out under the same conditions except for using the different kinds of catalysts, were compared with each other, so that it was confirmed that the copper/silica catalyst used in Example 6 had a highest catalytic activity. When compared with Comparative Example 1 in which the reaction was carried out based on Example 6 but without flowing hydrogen through the reaction system and without removing water in a liquid phase of the reaction system, it was confirmed, from the time required until completing the reaction or the amount of residual glycol after 8 hours elapsed from initiation of the reaction, that Examples 1 to 6 in which the reaction was carried out at a temperature of 230° C. using the catalyst in an amount of 5 parts by mass per 100 parts by mass of glycerol similarly to Comparative Example 6 but while removing water retained in the liquid phase, were enhanced in reactivity of glycerol, in particular, increased in reaction rate at a late stage of the reaction. In addition, it was also confirmed that Examples 1 to 6 exhibited a high selectivity to 1,2-PD. When comparing Example 6 with Comparative Example 1, it was confirmed that Example 6 was improved in the selectivity as compared to Comparative Example 1. From the results of Tables 3, 4 and 5, it was confirmed that even Examples 7 and 8 using a reduced amount of the copper/silica catalyst as well as Examples 10 and 11 using a low reaction temperature were improved in reactivity of glycerol, in particular, exhibited a high reaction rate at a late stage of the reaction, as compared to Comparative Example 1. Further, these Examples exhibited a high selectivity to 1,2-PD. In Example 9 in which the amount of the catalyst used was merely 1/10 time that of Comparative Example 1, the reaction rate became high at a late stage of the reaction, and the selectivity to 1,2-PD was also high. From the results of Tables 3 and 5, it was confirmed that when comparing Example 10 and Comparative Example 4 which were the same in both reaction temperature and amount of the catalyst used, the time required until completion of the reaction in Example 10 in which water was removed, was apparently shorter than that of Comparative Example 4, and Example 10 exhibited a higher selectivity to 1,2-PD than that of Comparative Example 4.

Examples 12 and 13

In Example 12, the hydrogenolysis reaction of glycerol was carried out in the same manner using the same copper-iron-aluminum-based catalyst as in Example 1 except that the hydrogen pressure within the reaction system was adjusted to 15 MPa. Whereas, in Example 13, the hydrogenolysis reaction of glycerol was carried out in the same manner as in Example 1 under a hydrogen pressure of 15 MPa similarly to Example 13 except for using a pulverized product of a copper/silica catalyst (product number: "F01B") available from Nikki Chemical Co., Ltd.

As shown in Table 6, it was confirmed that Examples 12 and 13 in which the reaction was carried out while removing water retained in the liquid phase of the reaction system, were improved in reactivity of glycerol as compared to that of Comparative Example 5, in particular, exhibited a high reaction rate at a late stage of the reaction, as well as Examples 12 and 13 also exhibited a high selectivity to 1,2-PD.

TABLE 6

| | Comparative Examples | |
| --- | --- | --- |
| | 5 | 6 |
| Catalyst | Cu/Silica | Cu/Silica |
| Amount of catalyst used (based on 100 parts by mass of glycerol) | 5 parts by mass | 5 parts by mass |
| Glycerol as raw material/water (molar ratio) | 1/0 | 1/20.5 |
| Reaction pressure (MPa) | 15.0 | 15.0 |
| Reaction temperature (° C.) | 230 | 230 |
| Flowing conditions of hydrogen — Flow rate (25° C., 0.1 MPa) / Flowing method | (Under hermetically sealed condition) | (Under hermetically sealed condition) |

| | Residual glycerol (mol %) | k ($h^{-1}$) | Amount of water in reaction liquid*1 | Residual glycerol (mol %) | k ($h^{-1}$) | Amount of water in reaction liquid*1 |
| --- | --- | --- | --- | --- | --- | --- |
| After reacted for 1 h | 50.5 | | 0.48 | 94.8 | | 21.54 |
| After reacted for 2 h | 29.3 | 0.54 | 0.71 | 85.1 | 0.11 | 21.36 |
| After reacted for 3 h | 16.7 | 0.56 | 0.78 | 83.2 | 0.02 | 21.49 |
| After reacted for 4 h | 10.4 | 0.47 | 0.84 | | | |
| After reacted for 5 h | 3.1 | 1.21 | 0.85 | 80.6 | 0.02 | 21.70 |
| After reacted for 6 h | 0.9 | 1.24 | 0.92 | 78.6 | 0.03 | 21.67 |
| After reacted for 7 h | | | | | | |
| After reacted for 8 h | | | | | | |
| After reacted for 10 h | | | | | | |
| Selectivity to final reaction products (mol %) — 1,2-PD | | 97 | | | 96 | |
| EG | | 3 | | | 4 | |
| Others and unknown substances | | 0 | | | 0 | |

| | Examples | |
| --- | --- | --- |
| | 12 | 13 |
| Catalyst | Cu—Fe—$Al_2O_3$ | Cu/Silica |
| Amount of catalyst used (based on 100 parts by mass of glycerol) | 5 parts by mass | 5 parts by mass |
| Glycerol as raw material/water (molar ratio) | 1/0 | 1/0 |
| Reaction pressure (MPa) | 15.0 | 15.0 |
| Reaction temperature (° C.) | 230 | 230 |
| Flowing conditions of — Flow rate (25° C., 0.1 MPa) | 5 L/min | 15 L/min |

TABLE 6-continued

| hydrogen | Flowing method | Introduced into liquid | | | Introduced into liquid | | |
|---|---|---|---|---|---|---|---|
| | | Residual glycerol (mol %) | k (h$^{-1}$) | Amount of water in reaction liquid*[1] | Residual glycerol (mol %) | k (h$^{-1}$) | Amount of water in reaction liquid*[1] |
| After reacted for 1 h | | 81 | | 0.20 | 42.4 | | 0.37 |
| After reacted for 2 h | | 50.8 | 0.47 | 0.34 | 13.8 | 1.12 | 0.37 |
| After reacted for 3 h | | 24 | 0.75 | 0.45 | 0.9 | 2.73 | 0.06 |
| After reacted for 4 h | | 8.1 | 1.09 | 0.40 | 0.1 | 2.20 | 0.03 |
| After reacted for 5 h | | 1.9 | 1.45 | 0.34 | | | |
| After reacted for 6 h | | 0.2 | 2.25 | 0.22 | | | |
| After reacted for 7 h | | | | | | | |
| After reacted for 8 h | | | | | | | |
| After reacted for 10 h | | | | | | | |
| Selectivity to final reaction products (mol %) | 1,2-PD | | 98 | | | 97 | |
| | EG | | 2 | | | 3 | |
| | Others and unknown substances | | 0 | | | 0 | |

Note
*[1]Amount of water in reaction liquid is the value assuming that a total amount of water generated from glycerol is 1.

Example 14

A 500 mL autoclave made of iron and equipped with a stirrer was charged with 10 g of a pulverized product of a copper/silica catalyst (product number: "F01B") available from Nikki Chemical Co., Ltd., and 200 g of glycerol, and an inside of the autoclave was purged with hydrogen. Further, hydrogen was introduced into the autoclave at room temperature until a hydrogen pressure therein reached 1 MPa. After the contents in the autoclave were heated to 230° C., the hydrogen pressure in the autoclave was raised until reaching 15 MPa, and then while keeping the autoclave in a hermetically sealed condition, the hydrogenolysis reaction was carried out for 2 h while maintaining a constant hydrogen pressure within the autoclave by compensating an amount of hydrogen consumed and decreased by the reaction. At this time, it was confirmed that 85.5 mol % of the glycerol added was reacted, and the proportion of water being present in the reaction solution was 0.93 assuming that a total amount of water generated from the glycerol was 1.

Thereafter, the contents in the iron autoclave was cooled to 150° C., and hydrogen was introduced into the reaction solution in the autoclave while keeping an inside pressure of the autoclave at 1.5 MPa and allowed to flow therethrough at a rate of 10 L/min (25° C., 0.1 MPa) to thereby remove water therefrom. Thereafter, the supply of hydrogen flowing through the autoclave was terminated, and the contents in the autoclave were heated to 230° C. and the hydrogen pressure within the autoclave was raised to 15 MPa. Then, the contents in the autoclave were subjected again to hydrogenolysis reaction under a hermetically sealed condition without flowing hydrogen therethrough while maintaining a constant hydrogen pressure within the autoclave by compensating an amount of hydrogen consumed and decreased by the reaction. The results are shown in Table 7.

As a result, it was confirmed that in Example 14 in which water was removed in the course of the reaction, the reactivity of glycerol after the removal of water was enhanced, and the selectivity to 1,2-PD was high, as compared to those of Comparative Example 5.

TABLE 7

| | Example 14 |
|---|---|
| Catalyst | Cu/Silica |
| Amount of catalyst used (based on 100 parts by mass of glycerol) | 5 parts by mass |
| Glycerol as raw material/water (molar ratio) | 1/0 |
| Reaction pressure (MPa) | 15.0 |
| Reaction temperature (° C.) | 230 |
| Flowing conditions of hydrogen upon removing water in the course of the reaction | Flow rate (25° C., 0.1 MPa): 10 L/min |
| | Flowing method: Introduced into liquid for 2 h after reducing the temperature and pressure from the time at which 2 hours elapsed from initiation of the reaction |

| | Residual glycerol (mol %) | k (h$^{-1}$) | Amount of water in reaction liquid*[1] |
|---|---|---|---|
| After reacted for 1 h | 31.8 | | 0.73 |
| After reacted for 2 h | 14.5 | 0.79 | 0.93 |
| Removal of water (for 2 h) | — | — | — |
| Upon initiating the reaction again | 8.1 | | 0.06 |

TABLE 7-continued

| | Example 14 | | |
|---|---|---|---|
| After 0.5 hour from the time of initiating the reaction again | 2.6 | 2.27 | 0.11 |
| After 1 hour from the time of initiating the reaction again | 0.7 | 2.62 | 0.11 |
| Selectivity to final reaction products (mol %) | 1,2-PD | 97 | |
| | EG | 3 | |
| | Others and unknown substances | 0 | |

Note
[1]Amount of water in reaction liquid is the value assuming that a total amount of water generated from glycerol is 1.

INDUSTRIAL APPLICABILITY

In accordance with the present invention, there is provided a process for producing a hydrogenolysis product of a polyhydric alcohol, in particular, producing 1,2-PD from glycerol, in an efficient manner by contacting the polyhydric alcohol with hydrogen in the presence of a hydrogenolysis catalyst while removing water being present in a liquid phase of the reaction system. In particular, when using the production process of the present invention, it is possible to convert glycerol in an efficient manner and produce 1,2-PD therefrom with a high selectivity under a low pressure condition which is advantageous for practicing industrial processes.

The invention claimed is:

1. A process for producing a hydrogenolysis product of a polyhydric alcohol by a batch method, comprising contacting and reacting a polyhydric alcohol with hydrogen in the presence of a hydrogenolysis catalyst in a reaction system,
while selectively removing water from a liquid phase of said reaction system,
to obtain said hydrogenolysis product of said polyhydric alcohol in said reaction system.

2. A process according to claim 1, wherein at any time between a time at which 60 mol % of said polyhydric alcohol in said liquid phase of said reaction system is reacted and a time at which said polyhydric alcohol is completely reacted, water present in liquid phase of the reaction system is removed such that a proportion of water present in said liquid phase of said reaction system is 0.5 or less assuming that a total amount of water generated from the polyhydric alcohol is 1.

3. A process according to claim 1, wherein said hydrogenolysis catalyst comprises copper.

4. A process according to claim 1, wherein said polyhydric alcohol is glycerol.

5. A process according to claim 4, wherein said hydrogenolysis product is 1,2-propanediol.

6. A process for according to claim 2, wherein said hydrogenolysis catalyst comprises copper.

7. A process according to claim 2, wherein said polyhydric alcohol is glycerol.

8. A process according to claim 7, wherein said hydrogenolysis product is 1,2-propanediol.

9. A process according to claim 3, wherein said polyhydric alcohol is glycerol.

10. A process according to claim 9, wherein said hydrogenolysis product is 1,2-propanediol.

11. A process according to claim 6, wherein said polyhydric alcohol is glycerol.

12. A process according to claim 11, wherein said hydrogenolysis product is 1,2-propanediol.

13. A process according to claim 3, wherein said hydrogenolysis catalyst is a copper-iron-aluminum catalyst, a copper/silica catalyst, a copper-zinc/titanium oxide catalyst, or a copper-Raney catalyst.

14. A process according to claim 6, wherein said hydrogenolysis catalyst is a copper-iron-aluminum catalyst, a copper/silica catalyst, a copper-zinc/titanium oxide catalyst, or a copper-Raney catalyst.

15. A process according to claim 1, wherein water is removed from said a liquid phase of said reaction system in the form of water vapor.

16. A process according to claim 1, wherein water is removed from said a liquid phase of said reaction system by adding a dehydrating agent to said reaction system.

* * * * *